United States Patent
Moenkemoeller

(10) Patent No.: US 9,709,498 B2
(45) Date of Patent: Jul. 18, 2017

(54) GAS-SENSOR ARRANGEMENT FOR DETECTING TARGET-GAS CONCENTRATION

(71) Applicant: paragon ag, Delbrueck (DE)

(72) Inventor: Ralf Moenkemoeller, Delbrueck (DE)

(73) Assignee: paragon AG, Delbrueck (DE)

( * ) Notice: Subject to any disclaimer, the term of this patent is extended or adjusted under 35 U.S.C. 154(b) by 0 days.

(21) Appl. No.: 14/792,794

(22) Filed: Jul. 7, 2015

(65) Prior Publication Data

US 2016/0018330 A1    Jan. 21, 2016

(30) Foreign Application Priority Data

Jul. 19, 2014    (DE) .................. 10 2014 010 712

(51) Int. Cl.
| | |
|---|---|
| *G01N 21/35* | (2014.01) |
| *G01N 21/61* | (2006.01) |
| *G01N 21/3504* | (2014.01) |
| *G01N 33/00* | (2006.01) |

(52) U.S. Cl.
CPC ......... *G01N 21/61* (2013.01); *G01N 21/3504* (2013.01); *G01N 33/004* (2013.01); *G01N 2201/061* (2013.01)

(58) Field of Classification Search
CPC .................. G01N 21/61; G01N 21/3504
See application file for complete search history.

(56) References Cited

U.S. PATENT DOCUMENTS

| | | | | |
|---|---|---|---|---|
| 5,468,961 A | * | 11/1995 | Gradon .............. | A61M 16/16 250/343 |
| 5,886,348 A | * | 3/1999 | Lessure ............ | G01N 21/3504 250/339.03 |
| 6,181,426 B1 | * | 1/2001 | Bender ............ | G01N 21/3504 356/432 |
| 2005/0038582 A1 | | 2/2005 | Arndt | |
| 2005/0269499 A1 | * | 12/2005 | Jones .............. | B08B 7/028 250/269.1 |
| 2014/0037506 A1 | * | 2/2014 | Miki .............. | G01N 21/783 422/84 |

* cited by examiner

*Primary Examiner* — Casey Bryant
(74) *Attorney, Agent, or Firm* — Andrew Wilford

(57) ABSTRACT

A gas-sensor arrangement for measuring a target-gas concentration has first and second NDIR emitters to one side of a space containing the target gas and projecting respective first and second beams of infrared light through the space. An it receiver on the other side of the space and irradiated by the first and second beams for emitting first and second outputs respectively corresponding to the first and second beams and together forming a receiver signal corresponding to radiation received from the first and second beams. One of the emitters is optically farther from the receiver than the other of the emitters. A filter between the receiver and the space is traversed by the first and second beams and permeable only to radiation of a wavelength range corresponding to the target gas. A controller connected to the radiation receiver calculates the target-gas concentration on the basis of the receiver signal.

12 Claims, 1 Drawing Sheet

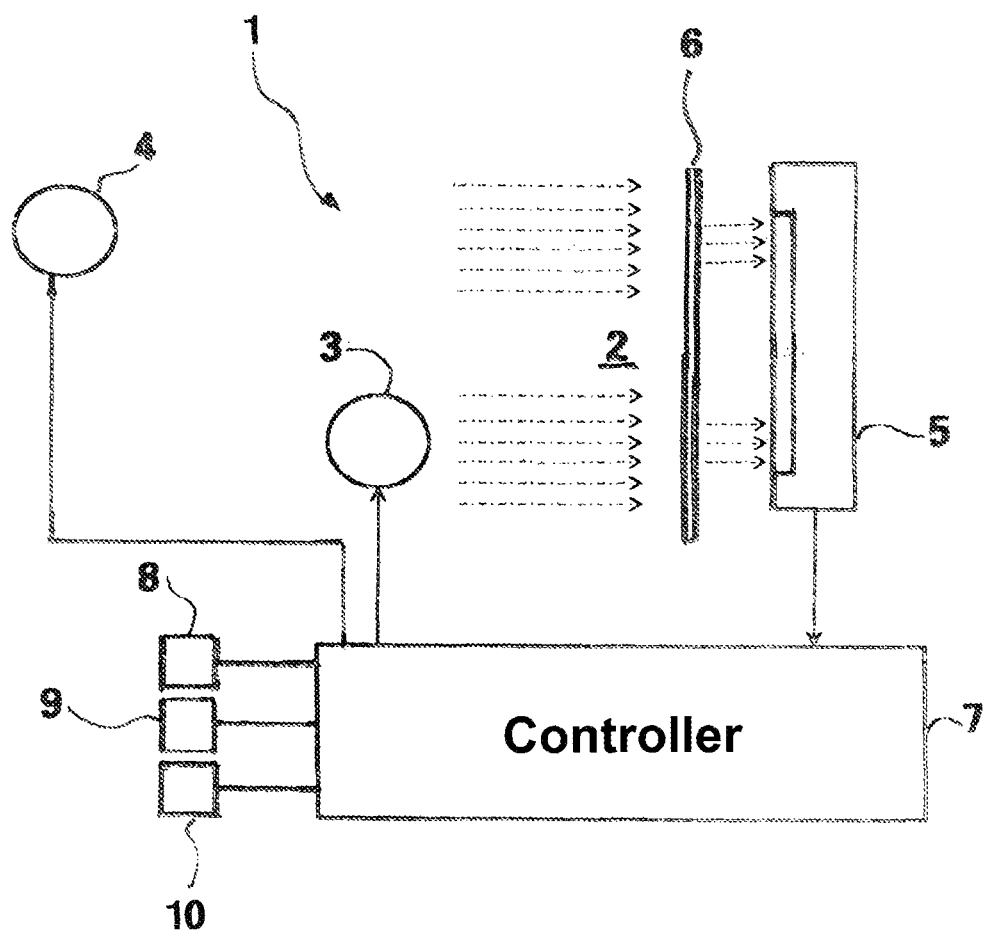

GAS-SENSOR ARRANGEMENT FOR DETECTING TARGET-GAS CONCENTRATION

FIELD OF THE INVENTION

The present invention relates to a gas sensor arrangement. More particularly this invention concerns such an arrangement for detecting a target-gas concentration.

BACKGROUND OF THE INVENTION

The invention relates to a gas-sensor arrangement for measuring a target-gas concentration with a radiation emitter, by means of which radiant energy can be projected through a space containing the target gas, a radiation receiver, by means of which radiant energy projected by the radiation emitter can be detected, a filter that is assigned to the radiation receiver and that is permeable to radiation of a wavelength range corresponding to the target gas, and a controller that is connected to the radiation receiver and by means of which the target-gas concentration can be calculated on the basis of a detector signal applied by the radiation receiver to the controller.

Such gas-sensor arrangements are increasingly being used to monitor air quality, wherein in particular the quality of outdoor air and/or the quality of air present in internal spaces, in particular also passenger compartments of vehicles, is monitored.

For the monitoring of air quality in internal spaces, it should be ensured that any deterioration in this air quality can be responded to with suitable measures.

In the area of vehicles, use has for some time been made of gas-sensor arrangements suitable for this purpose, which include metal oxide sensors (MOS), by means of which the air is monitored for the presence of VOC (volatile organic compounds). In the case of excessively high concentrations of these VOC in the air present in the passenger compartment of the vehicle, it is possible by using such gas-sensor arrangements for the vehicle ventilation system to be switched on automatically in order to provide an exchange of air.

Use is increasingly being made of air-conditioning systems in motor vehicles, wherein carbon dioxide ($CO_2$) is used as a refrigerant. Since carbon dioxide, when its concentration increases in the passenger compartment air, can lead to tiredness and sleepiness on the part of the vehicle driver, gas-sensor arrangements are also used to monitor leakages in the air-conditioning system. In these cases, the gas-sensor arrangement constituted as a $CO_2$ sensor arrangement is intended, in the case inadmissible $CO_2$ concentrations in the passenger compartment air, to trigger an alarm or to act on a control device of a vehicle ventilation system with the aim of eliminating the hazard due to an excessively high $CO_2$ content in the passenger compartment air. This could be brought about for example by increasing the air throughput in the vehicle passenger compartment, as a result of which the $CO_2$ concentration inside the vehicle passenger compartment is reduced.

A method for monitoring the air quality in a vehicle passenger compartment is known from DE 10 2004 024 2841 [US 2005/0038582], wherein a hazard prevention for living creatures that are present in the passenger compartment of a parked car is intended to be provided by a gas-sensor arrangement suitable for detecting $CO_2$. Here, the passenger compartment temperature is also monitored apart from the $CO_2$ content of the passenger compartment air. If, in the presence of a comparatively high passenger compartment temperature, a predefined $CO_2$ increase gradient is detected, it is assumed that a living creature, for example a child or a domestic animal, is present in the passenger compartment of a motor vehicle. Here, the $CO_2$ increase gradient is characteristic of the fact that breathing is occurring in the passenger compartment of the motor vehicle.

OBJECT OF THE INVENTION

Proceeding from the above-described prior art, the object of the invention is to provide a gas-sensor arrangement for measuring a target-gas concentration, that can be implemented with a comparatively low technical-structural outlay, and that can extremely reliably and accurately take measurements, especially under conditions in which measurements for hazard prevention are required.

SUMMARY OF THE INVENTION

According to the invention, this object is attained in fact that the gas-sensor arrangement is constituted as a nondispersive infrared spectrometry (NDIR) gas-sensor, that the radiation emitter of the NDIR gas-sensor arrangement comprises at least two infrared radiation emitters, and that each of the at least two infrared radiation emitters of the radiation emitter of the NDIR gas-sensor arrangement is disposed at a different optical spacing from the radiation receiver of the NDIR gas-sensor arrangement, the radiation receiver being constituted as an infrared radiation receiver. Alternatively, the solution can consist in the fact that, apart from the embodiment of the gas-sensor arrangement as an NDIR gas-sensor arrangement, the radiation receiver of the NDIR gas-sensor arrangement can comprise at least two infrared radiation receivers, and that each of the at least two infrared radiation receivers of the radiation receiver of the NDIR gas-sensor arrangement is disposed at a different optical spacing from the radiation emitter of the NDIR gas-sensor arrangement, the radiation emitter being constituted as an infrared source. Since the commercial outlay for radiation receivers is currently higher than that for radiation emitters, the embodiment of the NDIR gas-sensor arrangement according to the invention with two infrared radiation emitters and one infrared radiation receiver is at present preferred.

According to the invention, different measurement spacings are provided in the case of the NDIR gas-sensor arrangement, wherein the measurement spacing that is suitable in each case can be taken as a basis for the measurement depending on the requirement profile and the measurement purpose. A greater sensitivity and therefore a better resolution and accuracy in the case of low target-gas concentrations can be achieved with longer optical measurement spacings or path s. In the case of very high target-gas concentrations, however, the effect of a long optical path is that the gas-sensor arrangement enters as it were into a saturation state. Despite target-gas concentrations continuing to increase, a change in the infrared radiant energy received by the infrared radiation receiver is no longer possible with a comparatively low commercial outlay. The comparatively short optical path between the infrared radiation emitter and the infrared radiation receiver can be used for high concentrations. In turn, however, the latter is accompanied by a lower sensitivity and therefore a low resolution in the case of low target-gas concentrations. In the case of the NDIR gas-sensor arrangement according to the invention, a suitable operating mode can be achieved depending on the demands on the signal quality and according to detected target-gas concentrations.

Since the gas-sensor arrangement according to the invention is constituted as an NDIR gas-sensor arrangement, performance with a higher degree of reliability and accuracy can be guaranteed, since the cross-sensitivity of NDIR gas-sensor arrangements to gases not relevant to the measurement and in particular to air humidity is very small compared to other gas-sensor arrangements provided for the relevant applications here, in particular gas-sensor arrangements with metal oxide sensors.

The NDIR gas-sensor arrangement includes the infrared radiation emitter and the infrared radiation receiver. The filter sits in front of the infrared radiation receiver, the filter permitting only the wavelength of interest for the given measurement purpose to pass to the infrared radiation receiver. This wavelength is dependent on the target gas to be monitored. In the case of an NDIR gas-sensor arrangement for the detection of the $CO_2$ content, this wavelength lies for example at 4.26 μm, since one of the absorption bands of $CO_2$ lies here. If the NDIR gas-sensor arrangement is used for the monitoring of HC (hydrocarbons), a wavelength of for example 3.3 μm is selected.

The energy transmitted by the infrared radiation emitter to the infrared radiation receiver is measured by the infrared radiation receiver of the NDIR gas-sensor arrangement. When the target gas to be detected with regard to its concentration enters into the beam path between the infrared radiation emitter and the infrared radiation receiver, part of the radiant energy on the specific wavelength is absorbed by the target gas present in the radiation path. According to the Lambert-Beer law, amongst others, this absorption is dependent on the mean optical path length of the measurement spacing between the infrared radiation emitter and the infrared radiation receiver and on the concentration of the target gas. The Lambert-Beer law reads:

$$I = I_0 \cdot 10^{-\epsilon \cdot c \cdot d}$$

where
  $I_0$ the energy transmitted without target gas,
  c the target-gas concentration
  d the mean optical path length of the measurement spacing between the infrared radiation emitter and the infrared radiation receiver, and
  ε a constant dependent on the target gas.

Target-gas concentration c is determined according to the above-described formula. In the ideal case, $I_0$, d and ε are constant. In this case, it would be sufficient to measure transmitted energy I with the infrared radiation receiver and to determine target-gas concentration c with the aid of the formula. The higher the target-gas concentration c is, the less energy is transmitted. This is important, since all influences leading to a reduction in the energy transmission result in values for target-gas concentration c being outputted that are too high. A basic prerequisite for an exact measurement result is a radiant power of the infrared radiation emitter that is constant even over a very long period on the specific wavelength for the intended measurement. The mean optical path length of the measurement spacing between the infrared radiation emitter and the infrared radiation receiver must not change either.

If, for example, reflecting surfaces are used to increase the signal quality of the detector signal of the NDIR gas-sensor arrangement, so that a greater part of the radiant energy emitted by the infrared radiation emitter can focus on the infrared radiation receiver, it is of great importance that the reflection properties of the materials constituting the reflecting surfaces are stable and do not change even over a possibly protracted service live of the NDIR gas-sensor arrangement. A decrease in the reflexivity or also a decrease in the radiant power of the infrared radiation emitter would otherwise always be interpreted as an excessively high target-gas concentration. Depending on the use of the NDIR gas-sensor arrangement according to the invention, a false alarm could possibly be triggered in this case, which of course should be prevented.

It is known from the prior art, for example, to operate the infrared radiation emitter in a pulsed manner in order to reduce the ageing of the infrared radiation emitter of the NDIR gas-sensor arrangement and also to reduce the consumption of electrical energy of the NDIR gas-sensor arrangement. For example, it is sufficient for some applications and purposes for an updated measurement value to be available every 5 seconds. The infrared radiation emitter is then switched on only every 5 seconds until such time as it has reached its full radiant power. 500 to 1000 milliseconds are often sufficient for this purpose. Following a fixed time interval, the reception power at the infrared radiation receiver is then measured, wherein the target-gas concentration is determined from the detector signal resulting therefrom in the downstream controller.

If the NDIR gas-sensor arrangement is operated with a battery as a source of electrical energy, the pulsed operating mode known from the prior art is associated with a—for many applications—excessively high energy consumption. To solve this problem, provision is made in the case of the NDIR gas-sensor arrangement according to the invention such that the infrared radiation emitter of the NDIR gas-sensor arrangement can be operated with different powers. A considerable additional energy saving is thereby enabled.

Thus, for example, in the case where the NDIR gas-sensor arrangement is used for $CO_2$ leakage detection of a motor vehicle air conditioning system, an alarm threshold value is expedient and advisable that lies above a target gas or $CO_2$ concentration of 10000 ppm (1.0 volume-%). The upper limit of the measurement range advisable for these purposes then often lies above 100000 ppm (10.0 volume-%).

If it is to be detected whether a living creature is present inside an internal space, a wholly different measurement range of the NDIR gas-sensor arrangement is required than for the above-described $CO_2$ leakage detection of an air conditioning system. If the NDIR gas-sensor arrangement is used for the detection of the presence of living creatures inside an internal space, a high resolution and accuracy of the detection signal characterizing the $CO_2$ concentration in a concentration range up to 1000 ppm (0.1 volume-%) is required. This will be illustrated in the following example:

A sleeping infant draws breath approx. 20 times per minute. The air volume per breath amounts to approx. 100 ml. Per minute, the infant correspondingly exhales—with an enrichment of the respiratory air of 0.04 volume-% $CO_2$—0.08 l $CO_2$. In one hour, this is approx. 5 l $CO_2$.

If the internal space to be monitored has a volume of approx. 5 m³, i.e. 5000 l, the infant has caused an increase in the $CO_2$ concentration of 0.1 volume-% $CO_2$ after an hour. If it is assumed from this that a motor vehicle in the blazing sun reaches critical temperatures above 60 degrees C. in the passenger compartment within half an hour, the NDIR gas-sensor arrangement must be able to reliably detect an increase of the $CO_2$ concentration of 0.05 volume-% $CO_2$ (500 ppm). Without the operation of the infrared radiation emitter of the NDIR gas-sensor arrangement with different powers, as provided according to the invention, an NDIR gas-sensor arrangement known from the prior art would have a resolution that was far too low in a measurement range between 400 ppm and 5000 ppm.

To explain the advantages of the NDIR gas-sensor arrangement according to the invention, reference should additionally be made to the fact that one of the main energy consumers of such a NDIR gas-sensor arrangement is the infrared radiation emitter. For an NDIR gas-sensor arrangement with a particularly low energy consumption, therefore, the mode of operation of the infrared radiation emitter, such as it is known from the prior art, has to be changed. The pre-requisite for this is that the radiant energy received in the infrared radiation receiver of the NDIR gas-sensor arrangement is proportional to the radiant energy projected by the infrared radiation emitter. The radiant energy projected by the infrared radiation emitter is in turn directly dependent on the electrical energy used to operate the infrared radiation emitter.

A comparatively large amount of projected radiant energy thus also signifies a comparatively high amount of received radiant energy and therefore a comparatively large or distinct detector signal of the infrared radiation receiver. Such a comparatively large detector signal improves the signal-to-noise ratio, so that the measurement result is more accurate and has a better resolution.

Radiant energy W transmitted by the infrared radiation emitter to the infrared radiation receiver is proportional to the product of projected power $I_0$ and radiation duration T. In order to improve the signal quality, the projected power and/or the radiation duration could be increased. In order to reduce the energy consumption of the NDIR gas-sensor arrangement, the radiant power and/or the radiation duration could be reduced. Here, the size of the reduction could be worked out until the detector signal emitted by the infrared radiation receiver just still met the imposed requirements with regard to resolution, accuracy and signal-to-noise ratio. For this purpose, the NDIR gas-sensor arrangement according to the invention comprises a controller, by means of which the infrared radiation emitters of the infrared radiation emitter can be operated with different radiant powers. For this purpose, a voltage supply provided for the energy supply of the infrared radiation emitters can be adjustable, wherein the adjustment takes place by the controller. Various steps of the radiant power of the infrared radiation emitters can be adjusted via the level of the given operating voltage of the voltage supply.

Advantageously in the case of the NDIR gas-sensor arrangement according to the invention, the optical spacing between a first infrared radiation emitter and the infrared radiation receiver or the infrared radiation emitter and a first infrared radiation receiver is comparatively small and the optical spacing between a second infrared radiation emitter and the infrared radiation receiver or the infrared radiation emitter and a second infrared radiation receiver is comparatively large. As a result, a comparatively accurate measurement result can be achieved both in the case of very small and also very large target-gas concentrations or target-gas concentration changes to be detected.

In the case of the NDIR gas-sensor arrangement according to the invention, all the present infrared radiation emitters can advantageously be operated with different powers, so that the range in which exact measurements can be provided with a high degree of reliability is further increased.

The NDIR gas-sensor arrangement according to the invention can expediently be operated in at least two operating modes, wherein the first infrared radiation emitter is operated with a very low power in a first operating mode and the second infrared radiation emitter is operated with a high power in a second operating mode. The NDIR gas-sensor arrangement according to the invention has a comparatively low energy consumption in the first operating mode. In this operating mode, a reduced signal quality and therefore sacrificing a comparatively high resolution, accuracy and signal-to-noise ratio is consciously accepted. The comparatively low energy consumption has priority in this operating mode.

In the second operating mode, the NDIR gas-sensor arrangement according to the invention is operated with a comparatively high energy consumption. In this second operating mode, the priority is placed on a comparatively high quality of the detector signal, i.e. on a high resolution, a high accuracy and a high signal-to-noise ratio thereof.

According to an advantageous development of the NDIR gas-sensor arrangement according to the invention, the latter can also be operated in a third operating mode, wherein the second infrared radiation emitter is operated with a possibly much higher power compared to that in the first operating mode. For comparatively low target-gas concentrations, an exact detection of these target-gas concentrations or an increase in these target-gas concentrations is thus ensured.

As already mentioned above, it is known from the prior art to operate the infrared radiation emitter of the NDIR gas-sensor arrangement at intervals in order to reduce the energy consumption of the latter. If a low measuring rate is sufficient, the infrared radiation emitter is switched on briefly just to carry out each individual measurement. The infrared radiation emitter is switched off between the measurements and does not therefore require any electrical energy. The known interval operation also has the advantage that, during the times when the infrared radiation emitter is switched off, the signal of the infrared radiation receiver of the NDIR gas-sensor arrangement can be detected as a reference point for the following signal evaluation.

As already mentioned, there are applications in which a minimal energy consumption has to be achieved with a predetermined minimum measuring rate, for example in the case of the $CO_2$ leakage detection of an air conditioning system, which is operated with $CO_2$ as a refrigerant, in a parked motor vehicle. Here, the alarm threshold lies for example at a $CO_2$ concentration of 30000 ppm in the passenger compartment air of the motor vehicle. The alarm should be triggered at the alarm threshold value, with a permitted inaccuracy of a few percent. The basic content of $CO_2$ in the air stands at approx. 380 ppm. In a passenger car occupied by several occupants or persons, the $CO_2$ concentration can also reach values of 1900 ppm. The spacing from the above-described alarm threshold value of approx. 30000 ppm, however, is in any event still marked. The factor is greater than 15 in the example described above.

By way of example, the mean current consumption of 50 µA at 12 V DC (W=0.6 M WH) must not be exceeded in a parked motor vehicle in the rest mode. At the same time, however, a minimum measuring rate of one measurement per minute should be achieved. Only 0.6 m WH/60=0.01 mWH of electrical energy is thus unavailable for each measurement. An infrared radiation emitter with a nominal power of 400 mW could be operated for 90 ms with this available electrical energy. A typical infrared radiation emitter when used for NDIR, however, reaches its operating temperature and therefore its full radiant power only after several 100 milliseconds. The reduction in the radiation duration of for example 300 ms in the already described second operating mode to 90 ms in the already described first operating mode thus means a marked reduction in the radiant power and therefore a marked reduction in the signal quality. The required measurement tolerances in respect of the alarm threshold value thus cannot be achieved. The achievement of these measurement tolerances is achieved with the NDIR gas-sensor arrangement according to the invention solely by the fact that the infrared radiation emitter of the NDIR gas-sensor arrangement can be operated with different powers.

According to an advantageous development of the NDIR gas-sensor arrangement according to the invention, provision is made such that the NDIR gas-sensor arrangement can be switched from the first operating mode into the second operating mode by its controller depending on detector signals detected in the latter in the first operating mode of the NDIR gas-sensor arrangement.

The switch from the first into the second operating mode can be provided particularly when it is detected in the controller that a presettable threshold value of the target-gas concentration is reached or exceeded.

According to a further expedient development of the NDIR gas-sensor arrangement according to the invention, the latter can be switched by its controller from the first operating mode into the second operating mode when it is detected in the controller that a presettable threshold value of the gradient or the increase in the target-gas concentration is reached or exceeded.

For hazard prevention, it may expediently be advantageous to put an alarm system and/or a ventilation device or suchlike into operation by the controller of the NDIR gas-sensor arrangement if, in the second operating mode of the NDIR gas-sensor arrangement, it is detected in its controller that a presettable alarm threshold value is reached or exceeded.

In order to ensure that the NDIR gas-sensor arrangement according to the invention is operated, whenever reasonably possible, in its first operating mode accompanied by a low energy consumption, it is advantageous if the NDIR gas-sensor arrangement according to the invention can be put back from its second into its first operating mode by its controller if, in the second operating mode of the NDIR gas-sensor arrangement, it is detected by the controller that the threshold value set for the switch from the first into the second operating mode of the NDIR gas-sensor arrangement or another threshold value set for a switch from the second into the first operating mode is reached or fallen below.

In order to prevent constant switching from the first into the second operating mode and vice versa in certain applications, it is advantageous if the threshold value presettable for the first operating mode for switching into the second operating mode and the threshold value for the second operating mode for switching into the first operating mode of the NDIR gas-sensor arrangement can be adapted by the controller of the NDIR gas-sensor arrangement according to the invention if, in the second operating mode of the NDIR gas-sensor arrangement, it is detected by the controller that the presettable alarm threshold value is not reached during a presettable period following the switch from the first into the second operating mode of the NDIR gas-sensor arrangement.

In order to ensure, after a motor vehicle has been parked, both reliable $CO_2$ leakage monitoring as well as a reliable detection of any living creature present in the passenger compartment of the motor vehicle, it is advantageous if the NDIR gas-sensor arrangement according to the invention, after a vehicle equipped therewith for the monitoring of its passenger compartment has been parked or switched off, can be operated for a presettable period in an adjustable ratio intermittently between its first operating mode and its third operating mode. Any $CO_2$ leakage can reliably be detected by the detector signals detected in the first operating mode and the presence of a living creature in the passenger compartment of the motor vehicle can be reliably ascertained with the detector signals available in the third operating mode.

An alarm system and/or a ventilation device or suchlike is expediently put into operation by the controller if, in the second and/or third operating mode of the NDIR gas-sensor arrangement, it is detected in its controller that a presettable alarm threshold value is reached or exceeded.

The alarm system and/or the ventilation device is advantageously put into operation in the third operating mode only when, by a temperature sensor, the exceeding of the presettable temperature threshold value is detected and relayed to the controller.

For the optimum operation of the NDIR gas-sensor arrangement according to the invention, it is expedient if, by means of its controller, the NDIR gas-sensor arrangement can be automatically set according to an algorithm defined by presettable periods and presettable threshold and alarm values for the detector signals.

The NDIR gas-sensor arrangement according to the invention described above can, as already explained above, be advantageously used for the detection of the $CO_2$ concentration or the HC concentration in the passenger compartment of a motor vehicle.

In a method according to the invention for the operation of an NDIR gas-sensor arrangement, preferably an NDIR gas-sensor arrangement in one of the embodiments described above, at least two operating modes of the NDIR gas-sensor arrangement are provided, wherein an infrared radiation emitter of the NDIR gas-sensor arrangement is operated with a different power in each operating state of the NDIR gas-sensor arrangement, and wherein a first infrared radiation emitter is operated with a low power in a first operating mode and a second infrared radiation emitter is operated with a high power in a second operating mode.

For the implementation of the method according to the invention described above for the operation of an NDIR gas-sensor arrangement, provision is expediently made such that switching of the NDIR gas-sensor arrangement from one operating mode into another is always carried out when presettable threshold values are reached or fallen below or exceeded.

BRIEF DESCRIPTION OF THE DRAWING

The invention is explained below in greater detail with respect to an embodiment and reference to the drawing whose sole FIGURE shows an embodiment of a gas-sensor arrangement according to the invention for measuring a target-gas concentration in principle.

SPECIFIC DESCRIPTION OF THE INVENTION

The gas-sensor arrangement 1 shown in the single FIGURE is used to measure a target-gas concentration, for example inside a space 2. The space 2 can for example be a passenger compartment of a motor vehicle.

The gas-sensor arrangement 1 is constituted as a nondispersive infrared spectroscopy (NDIR) gas sensor and comprises a first infrared-radiation emitter 3 projecting infrared radiant energy through the space or passenger compartment 2 containing a target gas, for example carbon dioxide ($CO_2$).

Furthermore, the NDIR gas-sensor arrangement 1 comprises a second infrared radiation emitter 4 projecting infrared radiant energy through the space or passenger compartment 2 containing the target gas. The first infrared radiation emitter 3 and the second infrared radiation emitter 4, in the embodiment of the gas-sensor arrangement 1 according to the invention shown in the single FIGURE, constitute its radiation emitters.

An infrared radiation receiver 5 is provided spaced from the first infrared radiation emitter 3 of the NDIR gas-sensor arrangement 1. Infrared radiant energy projected by first infrared radiation emitter 3 through space or passenger compartment 2 can be detected by infrared radiation receiver 5.

In the embodiment of NDIR gas-sensor arrangement 1 represented in the single FIGURE, the spacing between the second infrared radiation emitter 4 and the infrared radiation receiver 5 is much greater than the spacing between the first infrared radiation emitter 3 and the infrared radiation receiver 5.

Lying in the radiation path between the infrared radiation emitters 3, 4 on the one hand and the infrared radiation receiver 5 on the other hand is a filter 6 that is connected to the infrared radiation receiver 5 and is designed to be permeable to radiation of a wavelength range that corresponds to the target gas. In this regard, a wavelength range of approx. 4.26 µm is selected in the case where $CO_2$ is the target gas, since one of the absorption bands of $CO_2$ lies here. If hydrocarbons (HC) are present as the target gas, a wavelength range of for example 3.3 µm is selected for this purpose.

Both the infrared radiation emitters 3, 4 and the infrared radiation receiver 5 of the NDIR gas-sensor arrangement 1 are connected to a controller 7. The target-gas concentration can be calculated in this controller 7 on the basis of a detector signal that is applied by the infrared radiation receiver 5 to the controller 7.

Moreover, the controller 7 of the NDIR gas-sensor arrangement 1 can operate the infrared radiation emitters 3, 4 with different powers.

Furthermore, in the illustrated embodiment, an alarm system 8 and a ventilation device 9 are connected to the controller 7 of the NDIR gas-sensor arrangement 1. If the value determined for the target-gas concentration in controller 7 exceeds a presettable limiting value, the alarm system 8 is operated by the controller 7 so that hazards to persons present in the space or passenger compartment 2 can be reduced or prevented. In addition or alternatively, the controller 7 can also put the ventilation device 9 into operation when the limiting value is reached or exceeded such that the target-gas concentration inside the space or inside the passenger compartment 2 can be brought back into a permitted range by operation of the ventilation device 9.

Furthermore, a temperature sensor 10 is connected to the controller 7 of the NDIR gas-sensor arrangement 1. The temperature in the space or passenger compartment 2 is detected by the temperature sensor 10. Triggering of the alarm system 8 and/or ventilation device 9 by the controller 7 can be carried out when a specific temperature threshold value is reached. For example, in a parked motor vehicle, the alarm system 8 or ventilation device 9 can thus be triggered only when a specific minimum temperature level is reached or exceeded.

In the illustrated embodiment, the NDIR gas-sensor arrangement 1 shown in the sole FIGURE can be operated in three different types of operation or operating modes. In a first operating mode, the NDIR gas-sensor arrangement 1 is operated with comparatively low energy. In this first operating mode, a reduced signal quality and therefore sacrificing of a comparatively high resolution, accuracy and signal-to-noise ratio is consciously accepted. The advantage of this first operating mode is its comparatively low energy consumption. In this first operating mode, the second infrared radiation emitter 4 is operated with low radiant power.

In a second operating mode, the NDIR gas-sensor arrangement 1 is operated with a comparatively high energy. In this second operating mode, priority is placed on a comparatively high signal quality with high resolution, high accuracy and high signal-to-noise ratio. In this second operating mode, the first infrared radiation emitter 3 is operated with high radiant power.

In a third operating mode, the NDIR gas-sensor arrangement 1 is also operated with comparatively high energy. In this third operating mode, priority is also placed on comparatively high signal quality with high resolution, high accuracy and high signal-to-noise ratio. In this third operating mode, the second infrared radiation emitter 4 is operated with a higher radiant power than that of the first operating mode.

The sensitivity of the above-described NDIR gas sensor 1 according to the invention is dependent, according to the Lambert-Beer law, amongst others, on the mean optical path length between the infrared radiation emitters 3, 4 and the infrared radiation receiver 5. A longer optical path means a higher sensitivity and therefore better resolution and accuracy with comparatively low target-gas concentrations. In the case of very large target-gas concentrations, however, the effect of a long optical path is that an NDIR gas sensor 1 enters as it were into saturation. Despite increasing concentration, a change in the infrared radiant energy received by the infrared radiation receiver 5 can no longer be measured acceptably.

A comparatively short optical path between the first infrared radiation emitter 3 and the infrared radiation receiver 5 is thus used for measurement at high target-gas concentrations. However, this comparatively short optical path length in turn causes a comparatively low sensitivity and therefore a very low resolution of the detector signal with comparatively low target-gas concentrations.

In the case of the NDIR gas-sensor arrangement 1 according to the invention, therefore, the first and second infrared radiation emitters 3, 4 are positioned such that, as described above, the first infrared radiation emitter 3 is at a relatively small spacing from the infrared radiation receiver 5 and the second infrared radiation emitter 4 is at a relatively large spacing therefrom.

In the first operating mode of the NDIR gas-sensor arrangement, the second infrared radiation emitter 4 having the large spacing from the infrared radiation receiver 5 is operated by the controller 7 with low power. As a result of the higher sensitivity on account of the long optical path between the second infrared radiation emitter 4 and the infrared radiation receiver 5, it is possible to carry out a reliable $CO_2$ leakage detection without the NDIR gas-sensor arrangement 1 having high energy consumption.

In the second operating mode, the first infrared radiation emitter 3 is operated by the controller 7 with high power. Since high signal quality with high resolution, high accuracy and high signal-to-noise ratio is thus made possible, a low target-gas concentration can be readily detected in this operating mode. The NDIR gas-sensor arrangement 1 can therefore detect whether a living creature is present in a parked vehicle. For this application, high resolution of the detector signal and high accuracy of the $CO_2$ concentration in the range up to 2000 ppm are required. In combination with a maximum permitted temperature level registered in the controller 7, the alarm system 8 or the ventilation device 9 can then always be put into operation if the NDIR gas-sensor arrangement 1 detects that a living creature is in a parked vehicle and that the temperature in the passenger compartment 2 of the motor vehicle exceeds a critical level.

A sleeping infant draws breath approx. 20 times per minute. The air volume per breath amounts to approx. 100 ml. Per minute, an infant thus exhales 0.08 l $CO_2$. In one hour, this is approx. 5 l. If passenger compartment 2 has a volume of approx. 5 $m^3$, the sleeping infant has produced an increase in the $CO_2$ concentration of 0.1 volume-% after an hour. Assuming that a parked motor vehicle in the blazing sun reaches critical temperatures above a level of 60 degrees C. in the passenger compartment 2 within half an hour, the NDIR gas-sensor arrangement 1 must be able to reliably detect an increase in the $CO_2$ concentration of 0.05 volume-% (500 ppm). In this regard, the third operating mode is in itself advantageous whereby the second infrared radiation emitter 4 located at a large spacing from the infrared radiation receiver 5, is operated with a high power. However, since monitoring for the presence of a living creature in the passenger compartment 2 of a motor vehicle takes place only when the motor vehicle is parked, it must be taken into account that the NDIR gas-sensor arrangement 1 needs to be operated with a low energy consumption.

Accordingly, after the motor vehicle has been parked for a predefined period, for example for 30 minutes, the NDIR gas-sensor arrangement is operated in the third operating mode. If the measured increase in the $CO_2$ concentration lies below a predefined threshold value during this period, the NDIR gas-sensor arrangement 1 changes into the first operating mode.

It is also possible for a predefined period after the vehicle has been parked, for the NDIR gas-sensor arrangement 1 to be operated intermittently between the first and the third operating mode. The ratio between the two operating modes can be freely programmed. For example, the NDIR gas-sensor arrangement can perform one measurement per minute in the first operating mode. This measurement is used for the $CO_2$ leakage detection. For a period of one hour after the vehicle has been parked, every tenth measurement is performed with the third operating mode. This measurement is then used for detecting the presence of living creatures in the passenger compartment of the motor vehicle. This procedure ensures rapid detection of $CO_2$ by the corresponding measurement in the minute interval. Furthermore, reliable detection of the presence of living creatures inside the passenger compartment 2 of the motor vehicle is provided within a sufficient time interval.

The NDIR gas-sensor arrangement 1 can expediently adjust the $CO_2$ monitoring if, within a pre-programmable time that can be stored in the controller 7, the increase in the $CO_2$ concentration lies below the limit defined for the detection of living creatures. The decision concerned can be taken internally, i.e. inside the NDIR gas-sensor arrangement 1, or by an external control device.

In the first operating mode of the NDIR gas-sensor arrangement, a presettable first threshold value of the target-gas concentration for the detection of $CO_2$ leakages can be stored in the controller 7. This first threshold value of the target-gas concentration is set so low compared to a likewise presettable alarm threshold value as to ensure, on account of the spacing between this first threshold value and the alarm threshold value, that switching from the first operating mode into the second operating mode takes place long before the alarm threshold value of the target-gas concentration is reached.

If, in the first operating mode of the NDIR gas-sensor arrangement, the controller 7 detects that the target-gas concentration reaches or exceeds the presettable first threshold value, the NDIR gas-sensor arrangement 1 is switched out of the first operating mode into the second operating mode takes place by the controller 7. The first infrared radiation emitter 3 is operated with a comparatively high radiant power in the second operating mode of the NDIR gas-sensor arrangement 1. This ensures that the quality of the detector signal emitted by infrared radiation receiver 5 to controller 7 is considerably improved in the second operating mode, and more precisely in a range of the target-gas concentration that lies well outside a hazard range.

If the target-gas concentration in the space or passenger compartment increases in the second operating mode of the NDIR gas-sensor arrangement 1 to the presettable alarm threshold value or if it exceeds it, the alarm system is operated by the controller 7 and the ventilation device 9 can be put into operation at the same time to ensure by ventilation of the space or passenger compartment 2 that a further increase in the target-gas concentration is prevented.

If, with the NDIR gas-sensor arrangement 1 running in the second operating mode, a third threshold value also presettable for the target concentration and storable in controller 7 is fallen below, the controller 7 switches the NDIR gas-sensor arrangement 1 back into the first operating mode.

If, after switching of the NDIR gas-sensor arrangement 1 into its second operating mode, the preset threshold value stored in the controller 7 is not reached, a new first threshold value is calculated that lies above the old first threshold value, and this new first threshold value is stored in the controller 7, after which the NDIR gas-sensor arrangement 1 is switched back into the first operating mode by the controller 7. Through this adaptation or increase in the first threshold value that is provided for switching the NDIR gas-sensor arrangement 1 out of its first into its second operating mode, the NDIR gas-sensor arrangement 1 is thus prevented from changing continually between the first and the second operating mode.

Operation of the NDIR gas-sensor arrangement 1 described above creates a situation whereby, for the overwhelming part of the service life thereof, its radiation emitter formed by the infrared radiation emitters 3, 4 can be operated with a very low electrical power requirement. The radiant power of the infrared radiation emitter 3, 4 of the NDIR gas-sensor arrangement 1 is increased only in the comparatively rare cases in which the presettable first threshold value of the target-gas concentration is exceeded. Only then is a detector signal with increased signal quality required, and this increased signal quality is ensured by the then considerably increased radiant power of the first infrared radiation emitter 3 of the NDIR gas-sensor arrangement 1.

The invention claimed is:

1. A gas-sensor arrangement for measuring a target-gas concentration, the arrangement comprising:
   first and second separate nondispersive infrared-radiation emitters to one side of a space containing the target gas and projecting respective first and second beams of infrared light from the one side through the space to the other side thereof;
   an infrared-radiation receiver on the other side of the space and having first and second parts each positioned to be irradiated by only a respective one of the first and second beams projected by the emitters through the space for emitting first and second outputs respectively corresponding to the first and second beams and together forming a receiver signal corresponding to radiation received from the first and second beams, one of the emitters being optically farther from the receiver than the other of the emitters;
a filter between the receiver and the space, traversed by the first and second beams, and permeable only to radiation of a wavelength range that corresponds to the target gas; and
a controller connected to the radiation receiver for calculating the target-gas concentration on the basis of the receiver signal.

2. The gas-sensor arrangement defined in claim 1, wherein an optical spacing between the first infrared radiation emitter and the first part of the infrared radiation receiver is shorter than an optical spacing between the second infrared radiation emitter and the second part of the infrared radiation receiver.

3. The gas-sensor arrangement defined in claim 2, wherein at least the second infrared radiation emitter can be operated with different power levels.

4. The gas-sensor arrangement defined in claim 1, wherein the controller is configured,
in a first operating mode, to operate the second infrared radiation emitter with low power, and,
in a second operating, to operate the first infrared radiation emitter with a power that is higher than that of the second infrared radiation emitter in the first operating mode.

5. The gas-sensor arrangement defined in claim 4, wherein the controller is configured,
in a third operating mode, to operate the second infrared radiation emitter with a higher power than in the first operating mode.

6. The gas-sensor arrangement defined in claim 4, wherein the controller is configured to switch between the first and second operating modes depending on the detector signals in the first operating mode or the second operating mode.

7. The gas-sensor arrangement defined in claim 6, wherein the controller is configured to switch from the first operating mode into the second operating mode on detection that a presettable threshold value set for switching from the first into the second operating mode of the nondispersive gas-sensor arrangement of the target-gas concentration is reached or exceeded.

8. The gas-sensor arrangement defined in claim 7, wherein the controller is configured to switch from the second operating mode into the first operating mode on, in the second operating mode of the NDIR gas-sensor arrangement, detection that the presettable threshold value or another threshold value set for switching from the second into the first operating mode is reached or fallen below.

9. The gas-sensor arrangement defined in claim 7, wherein the controller is configured to adjust a threshold value for the first operating mode for switching into the second operating mode or the presettable threshold value for the second operating mode on, in the second operating mode of the NDIR gas-sensor arrangement, detection by the controller that the presettable threshold value is not reached during a presettable period following switching from the first into the second operating mode of the NDIR gas-sensor arrangement.

10. The gas-sensor arrangement defined in claim 5, further comprising a vehicle having a passenger compartment forming the space, the controller, after the vehicle has been parked or switched off, operates for a presettable period in an adjustable ratio intermittently between its first operating mode and its third operating mode.

11. The gas-sensor arrangement defined in claim 4, further comprising
an alarm system and/or a ventilation device connected to the controller such that, in the second and/or third operating mode of the NDIR gas-sensor arrangement, the arrangement detects that a presettable threshold value of the target gas in the space is reached or exceeded.

12. The gas-sensor arrangement defined in claim 11, further comprising
a temperature sensor in the space and connected to the controller, the controller being configured to set the alarm system and/or the ventilation device into operation in the third operating mode only when the temperature sensor detects that a presettable temperature threshold value is present in the space.

* * * * *